(12) United States Patent
Stefanita et al.

(10) Patent No.: US 9,055,916 B2
(45) Date of Patent: Jun. 16, 2015

(54) MINIATURIZED THERMAL SYSTEM FORMED WITH SEMICONDUCTOR MATERIAL WITH MEDICAL APPLICATIONS

(71) Applicant: BioSignostix Inc., Burlington, MA (US)

(72) Inventors: Carmen-Gabriela Stefanita, Burlington, MA (US); Christopher Jonathan Zarowski, Burlington, MA (US)

(73) Assignee: BioSignostix Inc., Burlington, MA (US)

( * ) Notice: Subject to any disclaimer, the term of this patent is extended or adjusted under 35 U.S.C. 154(b) by 164 days.

(21) Appl. No.: 13/756,174

(22) Filed: Jan. 31, 2013

(65) Prior Publication Data

US 2014/0213928 A1    Jul. 31, 2014

(51) Int. Cl.
| | | |
|---|---|---|
| *A61B 5/00* | (2006.01) | |
| *A61B 18/08* | (2006.01) | |
| *A61F 7/00* | (2006.01) | |
| *A61B 5/04* | (2006.01) | |

(52) U.S. Cl.
CPC .............. *A61B 5/483* (2013.01); *A61B 18/08* (2013.01); *A61F 7/007* (2013.01); *A61B 5/685* (2013.01); *A61B 5/04001* (2013.01); *A61B 2562/028* (2013.01); *A61F 2007/0093* (2013.01); *A61F 2007/0095* (2013.01)

(58) Field of Classification Search
USPC ......................................................... 600/555
See application file for complete search history.

(56) References Cited

U.S. PATENT DOCUMENTS

| | | |
|---|---|---|
| 4,512,343 A | 4/1985 | Falk |
| 5,207,675 A | 5/1993 | Canady |
| 5,443,952 A | 8/1995 | Pestronk |
| 5,599,350 A | 2/1997 | Schulze |
| 7,044,950 B2 | 5/2006 | Yamamoto |
| 7,912,536 B2 | 3/2011 | Fendrock |

OTHER PUBLICATIONS

Nay et al., *A Voltage-Controlled Resistance with Wide Dynamic Range and Low Distortion*, IEEE Transactions on Circuits and Systems, vol. Cas-30, No. 10, pp. 770-772, Oct. 1983.

(Continued)

*Primary Examiner* — Brian Szmal
(74) *Attorney, Agent, or Firm* — Sunstein Kann Murphy & Timbers LLP

(57) ABSTRACT

In a first embodiment, a portable, battery-operated, minimally invasive small fiber neuropathy testing and diagnostic device, microcontrolled and interfacing with wireless powering to a wireless communications device is being disclosed. Said device is constructed out of an intra-epidermal thermal stimulus consisting of an electronically heated temperature-controlled polymer covered semiconductor material 101 lowered inside the skin through a probe 108 configured with three miniaturized electrodes 109 while a nerve impulse response measurement system records and identifies nerve action potential pulses through a proprietary algorithm. The invention also discloses a detection and characterization method of action potential pulses from neuron cells with respect to their timing such as pulse repetition statistics and rates from a single-point of measurement as diagnostically relevant for determining neuropathies. In an alternate embodiment, a medical device is constructed for biological tissue treatment for achieving a collagen denaturing effect or thermal tissue ablation.

15 Claims, 14 Drawing Sheets

(56) References Cited

OTHER PUBLICATIONS

Maluf et al., *A Thermal Signal Generator Probe for the Study of Neural Thermal Transduction*, IEEE Transactions on Biomedical Engineering, vol. 41, No. 7, p. 649-655, Jul. 1994.
Scharf et al., *Matched Subspace Detectors*, IEEE Transactions on Signal Processing, vol. 42, No. 8, pp. 2146-2157, Aug. 1994.
Okumura et al., *Numerical Computation of Thermoelectric and Thermomagnetic Effects*, IEEE, 17th International Conference on Thermoelectrics, 1998, pp. 89-92.
Sun et al., *Automatic Ultrasound Determination of Thermal Coagulation Front During Laser Tissue Heating*, IEEE, vol. 45, No. 5, pp. 1135-1146, Sep. 1999.
Gerstner et al., *Spiking Neuron Models: Single Neurons, Populations, Plasticity*, Cambridge University Press, 504 pages, 2002.
Massarweh et al., *Electrosurgery: History, Principles and Current and Future Uses*, Journal of American College of Surgeons, vol. 202, No. 3, pp. 520-530, Mar. 2006.
Izhikevich, *Dynamical Systems in Neuroscience: The Geometry of Excitability and Bursting*, The MIT Press, 210 pages, 2007.
Linear Technology Corporation, LT1920 Single Resistor Gain Programmable, Precision Instrumentation Amplifier, Linear Technology Corporation (1998), 1630 McCarthy Blvd., Milpitas, CA 95035-7417, 12 Pages.
H. Okumura, S. Yamaguchi, H. Nakamura, K. Ikeda, K. Sawada, Numerical Computation of Thermoelectric and Thermomagnetic Effects, IEEE 17th International Conference on Thermoelectrics 1998, pp. 89-92.
K. Nay, A. Budak, A voltage-Controlled Resistance with Wide Dynamic Range and Low Distortion, IEEE Transactions on Circuits and Systems 30 (10), Oct. 1983, pp. 770-772.
L.L. Scharf, B. Friedlander, Matched Subspace Detectors, IEEE Transactions on Signal Processing 42 (8), Aug. 1994, pp. 2146-2157.
N.I. Maluf, E.L. McNutt, S. Monroe, D.L. Tanelian, G.T.A Kovacs, A Thermal Signal Generator Probe for the Study of Neural Thermal Transduction, IEEE Transactions on Biomedical Engineering 41 (7), Jul. 1994, pp. 649-655.
Z. Sun, H. Ying, J. Lu, B. Bell, D.F. Cowan, M. Motamedi, IEEE Transactions on Ultrasonics, Ferroelectrics, and Frequency Control vol. 46, No. 5, Sep. 1999, all pages.
N. Massarweh, N. Cosgriff, D.P. Slakey, Electrosurgery: History, Principles and Current and Future Uses, Journal of American College of Surgeons, doi:10.1016/j.jamcollsurg.2005.11.017, all pages, published by Elsevier Inc.
W. Gerstner, W.M. Kistler, Spiking Neuron Models: Single Neurons, Populations, Plasticity, Cambridge University Press, 2002, all pages.
E.M. Izhikevich, Dynamical Systems in Neuroscience: The Geometry of Excitability and Bursting, The MIT Press, 2007.
LT1920 Single Resistor Gain Programmable, Precision Instrumentation Amplifier 1998 Linear Technology Corporation 1630 McCarthy Blvd., Milpitas, CA 95035-7417.

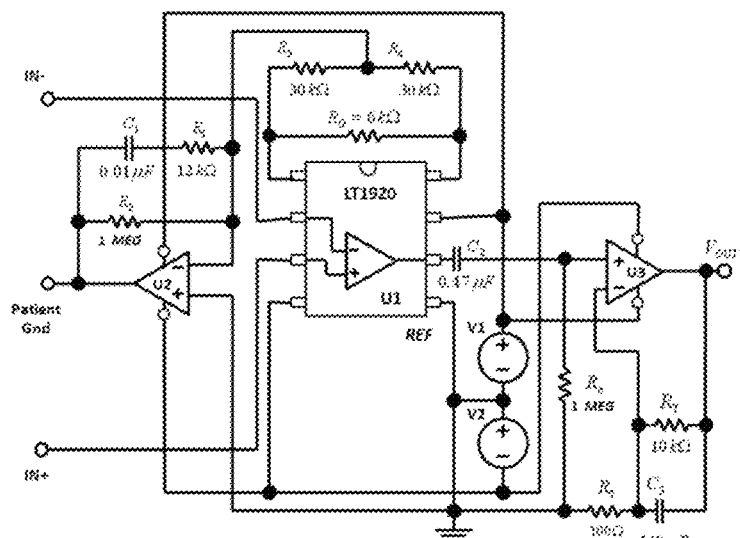
Fig. 13
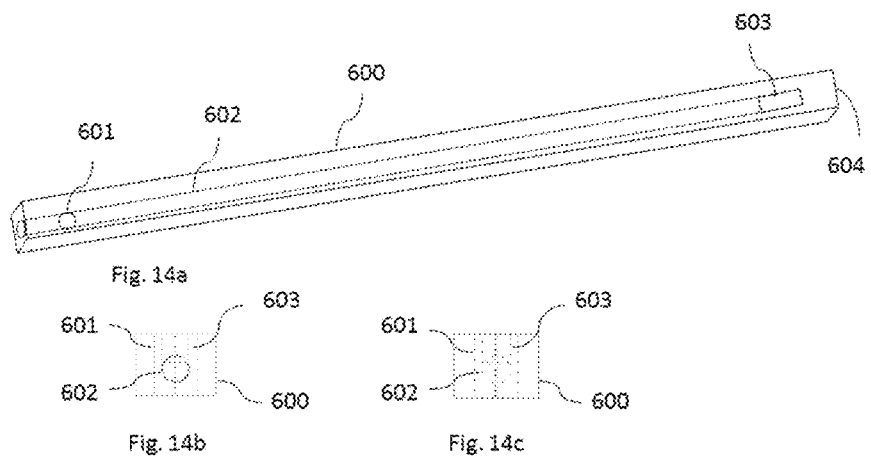
Fig. 14a
Fig. 14b
Fig. 14c

MINIATURIZED THERMAL SYSTEM FORMED WITH SEMICONDUCTOR MATERIAL WITH MEDICAL APPLICATIONS

CROSS-REFERENCE TO RELATED U.S. APPLICATION DATA

This application claims the benefit of the U.S. Provisional Patent Application No. 61/595,053 filed Feb. 4, 2012 by the present inventors. This provisional patent application is incorporated herein by reference.

BACKGROUND OF THE DISCLOSURE

A patient may have somatic symptoms such as burning pain in arms or feet, numbness in fingers or toes, electric shock-like or pins-and-needles sensations, reduced pin-prick or thermal sensation in the area of arms or feet. These symptoms are usually associated with small fiber neuropathy indicative of many illnesses such as diabetes, connective tissue disease, dysthyroid ophtalmopathy, HIV infection, hepatitis C, neurotoxic drug exposure, Lyme disease, paraneoplastic syndrome, vitamin B12 deficiency, celiac disease, lupus, as well as due to nerve injuries sustained in many professional sports or in military combat. Small fibers are a type of sensory nerve receptors that send signals to the brain and respond with a perception of pain if a potentially damaging thermal stimulus is acting. Thermal stimuli are detected by nerve endings called nociceptors, which are found in the epidermis and on internal surfaces such as the periosteum or joint surfaces. The concentration of nociceptors varies throughout the body, as they are found in greater numbers in the epidermis than in deep internal surfaces. All nociceptors are free nerve endings that have their cell bodies outside the spinal column in the dorsal root ganglia and are named according to their appearance at their sensory. Nociceptors have a certain threshold, that is, they require a minimum intensity of stimulation before they trigger a signal. Once this threshold is reached a signal is passed along the axon of the neuron into the spinal cord. Nociception has been documented in non-mammalian animals, including fishes and a wide range of invertebrates, including leeches, nematode worms, sea slugs, and fruit flies. As in mammals, nociceptive neurons in these species are typically characterized by responding preferentially to high temperature such as 40° Celsius or more, low pH, capsaicin, and tissue damage. The results of our experiments obtained with the technology disclosed in the present invention are a good indicator of what to expect in human subjects because the nerves in earthworms are unmyelinated like the C fibers in humans.

Slow pain is transmitted via slower type C fibers to laminae II and III of the dorsal horns, together known as the substantia gelatinosa. Impulses are then transmitted to nerve fibers that terminate in lamina V, also in the dorsal horn, synapsing with neurons that join fibers from the fast pathway, crossing to the opposite side via the anterior white commissure, and traveling upwards through the anterolateral pathway. These neurons terminate throughout the brain stem, with one tenth of fibres stopping in the thalamus and the rest stopping in the medulla, pons and periaqueductal grey of the midbrain tectum. Fast pain travels via type A-δ fibers to terminate in the dorsal horn of the spinal cord where they synapse on dendrites of the neospinothalamic tract. The axons of these neurons cross the midline (decussate) through the anterior white commissure and ascend contralaterally along the anterolateral columns. These fibers terminate on the ventrobasal complex of the thalamus and synapse with the dendrites of the somatosensory cortex. Fast pain is felt within a tenth of a second of application of the pain stimulus and is sharp and acute in response to thermal stimulation.

In general, a small fiber neuropathy is diagnosed either by biopsy or by elimination, after several other tests are performed to rule out or identify as co-existent other neuropathies. The commonly accepted practice as per recommendations of the U.S. Neurology Board is to diagnose small fiber neuropathies indirectly due to the lack of reliable techniques that can identify these types of neuropathies directly. Electromyograms (EMG) are the standard diagnostic technique for large fiber neuropathies and are used when the patient complains of neurological symptoms that may be due to small fiber, large fiber or a combination of fiber damage. However, preserved functions in small fiber neuropathy are motor strength, tendon reflexes, or proprioception; therefore techniques performed on large fibers do not give information about small fibers. Other diagnostic techniques are nerve conduction tests or quantitative sensory testing, both for large fibers and therefore not relevant to small fiber degeneration. Contact heat evoked potentials record electrical signals that are mostly from A-δ fibers and do not test intra-epidermal C fiber nerves. There is a need for objective investigations of nociceptor fiber loss or dysfunction to diagnose sensory small fiber neuropathy. Our testing technique disclosed in the present invention targets both C and Aδ fibers.

A nerve skin biopsy determines through microscope analysis the density of small fibers in the epidermis. The number of small fibers is counted per given volume of tissue. The technique involves inserting a biopsy needle into the arm or leg of the patient and removing enough tissue to be analyzed by a pathologist under the microscope. A regular neurology practice does not perform skin biopsies, and the patient is sent to a hospital for further diagnostic testing. Our technique disclosed in the present invention is more advantageous than a biopsy because it provides the opportunity of immediate test results with no waiting for results to be analyzed post-procedure and then mailed to the patient.

For the alternate embodiment of the present invention: In many surgical instruments, a high frequency electrical current passes through tissue to create a certain clinical effect. Whether they are for electrocautery, coagulation, or electrosurgery, the instruments have a common characteristic, namely production of heat and heat interaction with tissue. Heating effects produced by the surgical instrument determine the clinical outcome of the treatment of tissue. Coagulation of tissue is the result of protein denaturation due to cumulative heating which means that it is history dependent. As heating power is applied to the area, protein denaturation is determined by the amount of power and the duration of the application. Experience suggests that changes in tissue occur in the first few seconds of exposure to a certain level of heat. After some time, equilibrium is reached and coagulation finally occurs so that an irreversible change of tissue structure takes place. Specifically, below ~46° C. thermal damage to tissue is reversible. As tissue temperatures exceed 46° C. the proteins in the tissue become permanently denatured losing their structural integrity. Above 90° C. the liquid in the tissue evaporates resulting in significant dehydration.

Radiofrequency generators or ultrasound generators produce currents which induce ionic vibrations. These ionic vibrations cause intracellular heat that results in boiling (explosion) for cutting, or dehydration (dessication) and coagulation. Electrosurgical instruments based on high frequency electrical currents can devitalize tissue at the wound edges leaving dead tissue behind obstructing closure of wounds and predisposing wounds to post-operative infections. However, by slowly heating the tissue at an optimum temperature, a surgical wound can be closed without burning or scarring the surrounding tissue which is what the alternate embodiment of the present invention provides.

SUMMARY OF THE DISCLOSURE

A first embodiment discloses a testing device and method for aiding in the diagnosis of small fiber neuropathy related to determining the presence of small nerve fibers, unmyelinated C and thinly myelinated A-δ fibers that innervate intra-epidermal layers. A miniaturized thermal stimulus is lowered intra-epidermally into the patient's lower leg or arm via a needle-like encapsulation. The resistive Joule effect is a common method of obtaining heating in metals or other electrically conductive materials. However, as part of the present invention we disclose a new approach to obtaining heating based on generating a temperature change in materials that possess unusual thermal, electric, and/or magnetic properties due to the controlled manufacturing process and material composition. Some of these effects are thermoelectric in nature and are facilitated by junctions between dissimilar conducting materials allowing a thermal flux to be induced in the system composed of two conducting media. Other temperature changes can be induced in these materials due to the presence of a magnetic field, and these effects are known collectively as thermomagnetic effects, although more than one distinct effect can be identified depending on magnetic field orientation with respect to current flow. Other thermal effects specific to semiconductor materials also take place within the material when driven by certain electronic circuitry.

Our proprietary thermal stimulus and its electronic circuitry can for instance set a temperature under ~46° C. corresponding to a power level just below 0.8 $J/cm^2$, the known threshold that does not cause damage to tissue appropriate for patient testing. Lower levels of temperature can also be set and controlled, as needed. On the other hand, higher temperatures can also be achieved for other medical applications. The semiconductor material we use in our thermal stimulus is combined with certain electronic circuits so that the heating effect we obtain is based on more than one physical phenomenon. Special characteristics of the semiconductor material are exploited so that by the use of various thermal effects observable in certain types of semiconductors it delivers heat when driven by appropriate electronic circuitry.

The thermal stimulation inside the skin occurs for less than a second targeting small fiber nerves which create a neurological response in the brain. Heat flow is localized. A resulting nerve impulse response is recorded concurrently at this site of intra-epidermal thermal stimulation by using a bipolar nerve signal amplification via the three miniaturized electrodes 109 of which one is connected to patient ground. Accounting for amplifier gain of 1000 V/V the physiologically meaningful spikes are no more than about 100 microvolts. Data is collected and processed through a proprietary algorithm to reliably identify nerve action potential pulses in the presence of random noise signals and in the presence of interference due to power line hum. Digitization of signals occurs through a microcontroller which also interfaces to a host PC, a display screen or a wireless communications device.

The first embodiment of the present invention has the following advantages over the prior art:

Direct small nerve fiber stimulation:
No known diagnostic procedure uses a miniaturized thermal stimulus next to micron thin electrodes to stimulate directly small fibers intra-epidermally and record the nerve impulse response. At best, other techniques record a biopotential on the surface of the patient's skin from bundles of different fibers of different lengths. These techniques give only superficial, non-conclusive results from a mixture of nerve fiber population that can be obtained by running a needle on the skin of the patient. This is partly why our device emphasizes intra-epidermal insertion of stimulus and response sensing, to give a direct indication of small fiber response. The other reason for intra-epidermal insertion is to minimize signal interference from the environment during recording. Surface measurements are more susceptible to interference from external sources such as power lines (50 Hz or 60 Hz with harmonics).

Concurrent thermal stimulation of nerve fibers and recording of nerve impulse response:
The thermal stimulus, the type of neurons that we desire to characterize and the response sensing are all in close proximity of each other. Furthermore, the combination of point-source with point-measurement gives spatial resolution to the diagnostic device. The thermal stimulus properly deployed in the tissue will be in adequate proximity to where unmyelinated C fiber neurons are normally located. These neurons will respond to low-level heating in a range that cannot cause a burn generating action potentials (APs) which are sensed by the nerve impulse amplifier electrodes. Of course, the latter are in close proximity to the thermal stimulus, being part of the inserted subsystem. Signals output from the nerve impulse amplifier would be used to distinguish the normal from the abnormal neural responses.

Real time, objective data:
Provides quantitative rather than subjective nerve signal data (i.e. indication of pain by the patient) with real-time measurements.

A single-point of measurement as diagnostically relevant for determining small fiber neuropathies:
The detection and characterization method of action potential pulses from neuron cells from only a single-point of measurement shows differences with respect to their timing such as pulse repetition statistics and rates. The device is therefore useful in assessing nociceptive fiber loss or dysfunction in patients that may be suffering from diabetes, connective tissue disease, dysthyroid ophtalmopathy, HIV infection, hepatitis C, neurotoxic drug exposure, Lyme disease, paraneoplastic syndrome, vitamin B12 deficiency, celiac disease, or lupus.

Miniaturized thermal stimulator with good control of temperature level:
In addition to using the appropriate electronic circuitry to drive the semiconductor material, the magnitude of the delivered heat power density is also determined through choice of the material, its doping level, defect concentration, as well as its physical dimensions. Properties of semiconductor wafers can these days be manipulated through appropriate manufacturing conditions such that the material displays unique features depending on its doping level or defect concentration, especially for wafers thinner than 450-500 micrometers (µm). Our experimental results show interesting thermal effects happening within the material, including a negative temperature coefficient. This means that the resistance of the material decreases as temperature increases, correlating with an increased current into it. This is not just Joule heating as the latter is only $I^2R$ power (current I, resistance R), and will happen regardless of whether or not the temperature coefficient of resistance is negative or positive. Analysis of oscilloscope measurements data shows that there are correlations between the measured temperature sensor voltage and material specimen voltage values. The semiconductor material allows heating with small currents in the milliamperes range in small volumes of material, for instance only 500×500 micrometers ($\mu$m) or smaller. This is not resistive heating as in metals or coils. To obtain the same heating from the latter more material is required and larger electrical currents in the amperes range that would melt the electrode wires inserted into the patient. Running several amperes of current into intra-epidermally inserted sensor needles to power the thermal stimulator is not recommended. There is a safety issue such as fine wires melting from too much current. In the present invention, the electronics can be further designed to limit power flow into the thermal stimulator that a tissue burn simply cannot happen. Indeed, the present feedback control unit for temperature is part of this. However a current/voltage limiting circuit may be added for extra safety. Electrical isolation procedures, standard and known, exist to isolate the patient from a failure of the nerve impulse amplifier circuit.

Electrical insulation of patient from thermal stimulus:
The medical grade plastic covering the semiconductor material avoids sending an electrical current through the patient, but allows thermal flux to flow. It also provides sterilized contact with the patient's tissue.

Device portability:
Measurements at dc voltages of just a few volts show thermal effects not observed for ac kHz signals applied to the semiconductor material. This observation is important when considering how to power the semiconductor material to obtain heating effects. This means, dc voltages can be used to power the thermal stimulator. Also, the low dc voltage used in the other electronic circuits has the advantage that it can be generated by a high density battery, allowing portability of the whole medical device through usage of batteries. This is especially desirable when the device is operated in environments without direct access to electricity.

Disposable miniaturized electrodes:
The part that contacts tissue, such as the miniaturized electrodes 109 contained in probe 108 are intended to be disposable. The electronics is outside of that part of the device which introduces the electrodes and polymer covered semiconductor material 101 into the patient intra-epidermally. There is wiring from the electronics module to the miniaturized electrodes 109, polymer covered semiconductor material 101, and temperature sensor 104, however a wireless embodiment is currently planned. The wiring is rather fine, high gauge since current levels and voltages are small. It is possible to set up a recycling program to reclaim probe materials assuming this is economically meritorious. Disposable part is replaced with each procedure and contains the miniaturized electrodes 109 which are the input to the nerve impulse amplifier circuit, and the polymer covered semiconductor material 101. Polymer encapsulation is for electrical isolation but with good thermal conductivity.

The alternate embodiment of the present invention has the following advantages over the prior art:
Electrical insulation of patient:
Same reasons as for the first embodiment.
Good control of heating temperature:
Same reasons as for the first embodiment. Additionally, higher levels of heating can be achieved which could be used for tissue ablation. The laboratory setup implemented in the present invention permits temperatures up to about 120 Celsius. Heat flow is localized.

Device portability:
Same reasons as for the first embodiment.

Moderate, transient tissue heating:
For low levels of heating, achieves a collagen denaturing effect in biological tissue that may be used for skin or biological tissue treatment or as a medical device for wound closure.

Alternating currents (ac) are not needed to induce intracellular dehydration:
Only direct current or voltages (dc) are used to heat the instrument tip.

Market potential for the first embodiment of the present invention:
There are 143 Million people in the US over 40 of which many suffer from small fiber neuropathy or other forms of neuropathy. Peripheral neuropathy has a 10.5% incidence rate in adults of which 27.8% have small fiber neuropathy. With roughly 13,500 US neurologists, a target market are these neurologists, but we are also considering 230,000 US physician offices.

Market potential for the alternate embodiment of the present invention:
Wound care seems to have been performed on 12.9% of all emergency department visits. Of all visits, 3% of them were for skin and subcutaneous tissue diseases. Visits for lacerations and cuts of upper extremities constituted 2,347,000 in one year. The lacerations and cuts for the facial area alone amount to 1.7% of total emergency department procedures in one year. Injury-related lacerations and cuts of head and neck area as the primary reason for the emergency department visit constituted 2.1%. The technology described in the alternate embodiment could replace emergency department visits by performing wound closure or wound treatment tasks in a doctor's office instead of a hospital.

BRIEF DESCRIPTION OF THE DRAWINGS

FIG. 13 is a schematic drawing of a typical nerve signal amplifier circuit for amplifying voltages measured using miniaturized electrodes of the first embodiment of the present invention.

FIG. 14a is a view of half of clamp subsystem of an alternate embodiment of the present invention.

FIG. 14b is a left side view of FIG. 14a of an alternate embodiment of the present invention.

FIG. 14c is a right side view of FIG. 14a of an alternate embodiment of the present invention.

FIG. 20b represents processed experimental data obtained from a first embodiment of the present invention and illustrates an empirical distribution of the action potential pulse inter-arrival times for the data in FIG. 20a.

LIST OF PART NUMBERS

Figure 1:
FIG. 1 illustrates a perspective view of the polymer covered semiconductor material of the first embodiment of the present invention.

First Embodiment
101—polymer covered semiconductor material
102—silver paste
103—electrical wires
104—temperature sensor
105—thermally conductive paste
106—electrical wires for temperature sensor
107—encapsulation
108—probe
109—miniaturized electrodes
110—electrical wires for electrodes
Alternate Embodiment:
600—half of clamp
601—hole
602—through-hole
603—groove
604—clamp tip
700—cap
701—opening
702—magnet

DETAILED DESCRIPTION OF THE DISCLOSURE

The terms top, bottom, left, right and similar terms refer to the figure being discussed. Specific choices of electronic components in electronic circuits are for illustration and are not limiting unless otherwise stated. If a part number in the figures refers to multiple parts, only one or two parts may be assigned the part number, and the same part number may be used for the singular part and the same multiple parts in the figures. The same part number may be used for a generic term such as the polymer covered semiconductor material 101, a combination of elements such as narrow-gap semiconductor material from the III-V periodic table group or a specific material compound such as doped or undoped indium antimonide. Other material embodiments are possible, for example, the material can be replaced by a ceramic or a material with thermoelectric or thermomagnetic properties. The semiconductor material in the embodiments described herein is made by 5N Plus Trail Inc. 9200 Industrial Rd., Trail, British Columbia V1R 4X7, Canada. The material is a doped indium antimonide wafer with crystal ID NI090128, slice ID 73B, center thickness in microns 1007 μm, peak to valley in microns measured at 95% diameter PV 1.7 μm. The carrier concentration and mobility of this material measured at 77K are between cc=5.02-8.82E14 and mobility=3.22-3.26E5. The indium antimonide wafer is manufactured by the following process: 1. refine indium and antimony to minimum 99.99995% (6N5) purity; 2. Stoichiometrically fuse indium and antimony to form polycrystalline InSb; 3. Refine InSb to minimum 99.999995% (7N5) purity; 4. Load InSb feed material into crystal growth furnace with applicable amounts of tellurium as an n-type dopant; 5. Grow monocrystalline InSb by Czochralski process (for a description of this, see http://en.wikipedia.org/wiki/Czochralski_process); 6. Orient the crystal to applicable cut planes and cut wafers; 7. Circle the wafers to applicable diameter; 8. Polish wafers to customer specifications. The actual dimension of 101 in FIG. 1a is given by L1, where L1 is generally in the micrometer range of 100 μm to 500 μm, however can also be of different size (below 100 μm or above 500 μm).

First Embodiment

The first embodiment is intended to be used for human diagnostic testing of small nerve fibers whose endings are contained in the epidermis. Small fibers are a type of sensory nerve receptors that send signals to the brain and respond with a perception of pain if a potentially damaging thermal stimulus is acting. A thermal stimulus and sense electrodes are injected intra-epidermally through a disposable probe. The thermal intra-epidermal stimulus consists of the parts shown in FIGS. 1 through 2 and consists of an electronically heated temperature-controlled polymer covered semiconductor material 101 of micron dimensions, hence it is designated as a miniaturized thermal stimulus. Electronic heating of the polymer covered semiconductor material 101 occurs through a combination of thermoelectric, thermomagnetic or resistive heating, or may occur through only one of these effects. Temperature control of the polymer covered semiconductor material 101 to an accuracy of 1° C. is expected with today's temperature sensor technology but the nature of the application does not require great precision as long as it does not damage the tissue. Temperature is regulated to avoid a hazard. When the miniaturized thermal stimulus is applied to C nerve fiber or A-δ nerve fiber endings also known as small fiber endings (nociceptors), nerve cells from these small fibers respond to the thermal stimulus by sending action potential pulses through nerve axons. The thermal stimulation can be epidermal, intra-epidermal, intra-dermal, or hypo-dermal.

A form of digital signal processing is used to detect and count action potential pulses and determine timing of pulses. It is such information that is diagnostically useful. The subsystem comprised of all the parts shown in FIGS. 1 through 13 constitutes an analog subsystem because the output data of this system is an analog signal. A microcontroller collects and processes this analog signal and sends it to a display screen, a PC or a wireless handheld device such as a smartphone. As such, our device reaches a conclusion or a diagnosis on the spot. The user of this diagnostic instrument gets an instant response. Our device detects small fiber neuropathy directly and objectively, without subjective input from patients such as an indication of pain on a scale. The device can be sized and configured so that it is capable of being used as a minimally invasive small fiber neuropathy testing and diagnostic device.

Figure 1A:
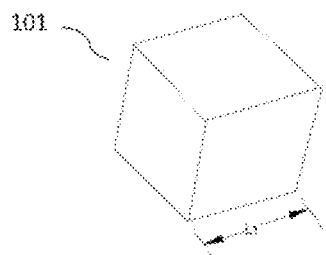
FIG. 1a is an enlarged drawing of an element of FIG. 1.
Figure 2:
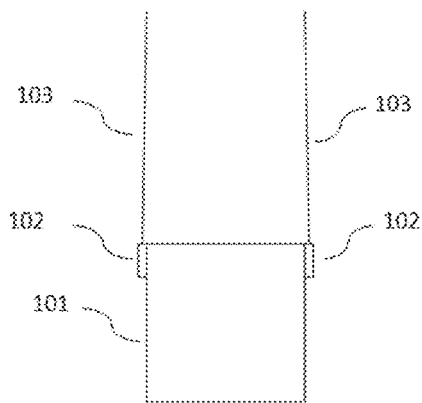
FIG. 2 is an illustration of a subsystem consisting of polymer covered semiconductor material, silver paste, and electrical wires of the first embodiment of the present invention.
Figure 3:
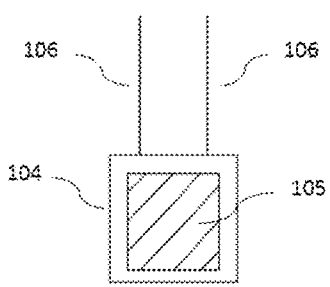
FIG. 3 illustrates a subsystem consisting of temperature sensor, thermally conductive paste and electrical wires for temperature sensor of the first embodiment of the present invention.
Figure 4:
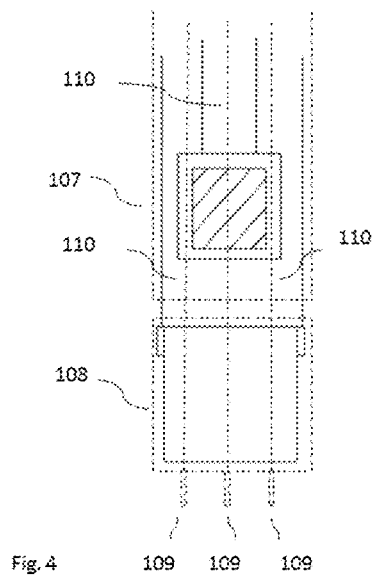
FIG. 4 illustrates a subsystem consisting of encapsulation, temperature sensor, probe with miniaturized electrodes, electrical wires for electrodes and polymer covered semiconductor material of the first embodiment of the present invention.
Figure 5:
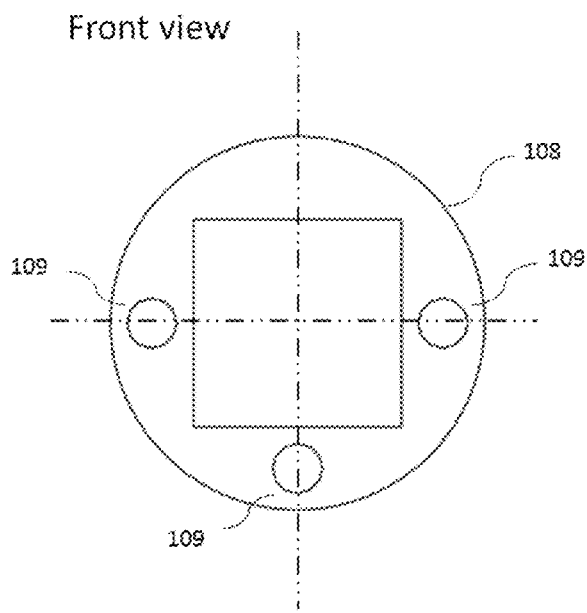
FIG. 5 is a top view a subsystem consisting of a probe and miniaturized electrodes of the first embodiment of the present invention.
Figure 6:
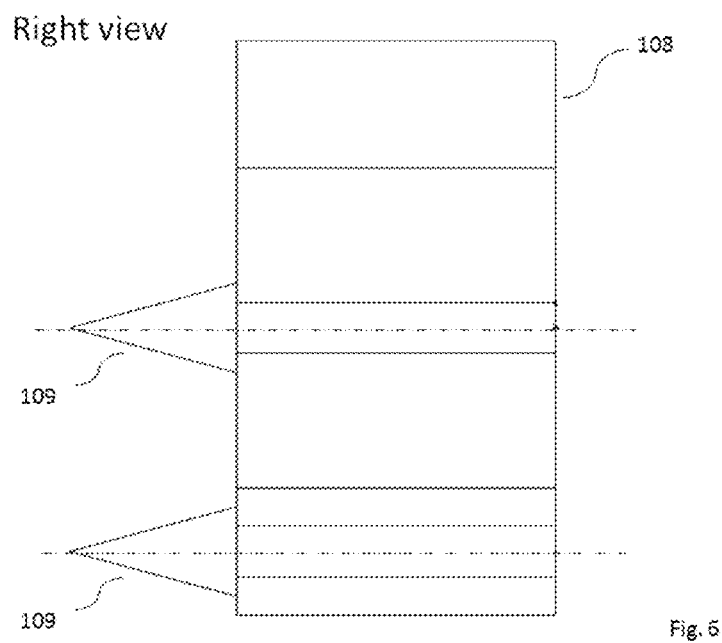
FIG. 6 is a right side view of FIG. 5.
Figure 7:
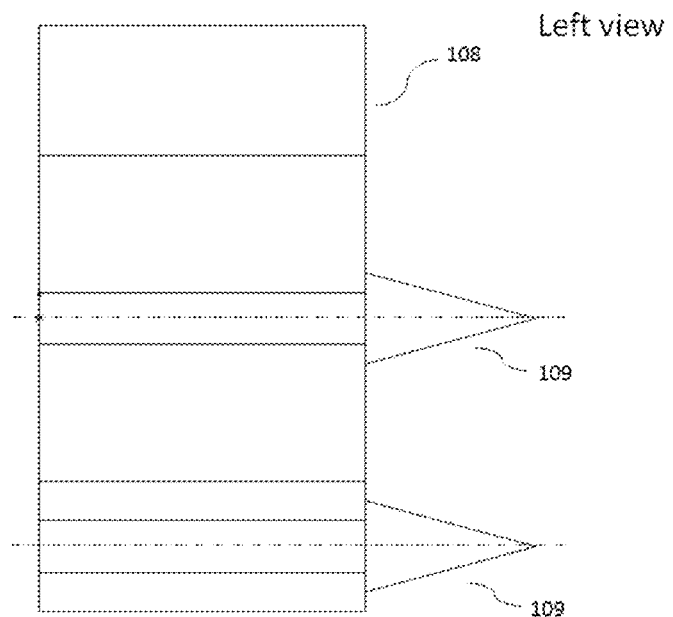
FIG. 7 is a left side view of FIG. 5.
Figure 8:
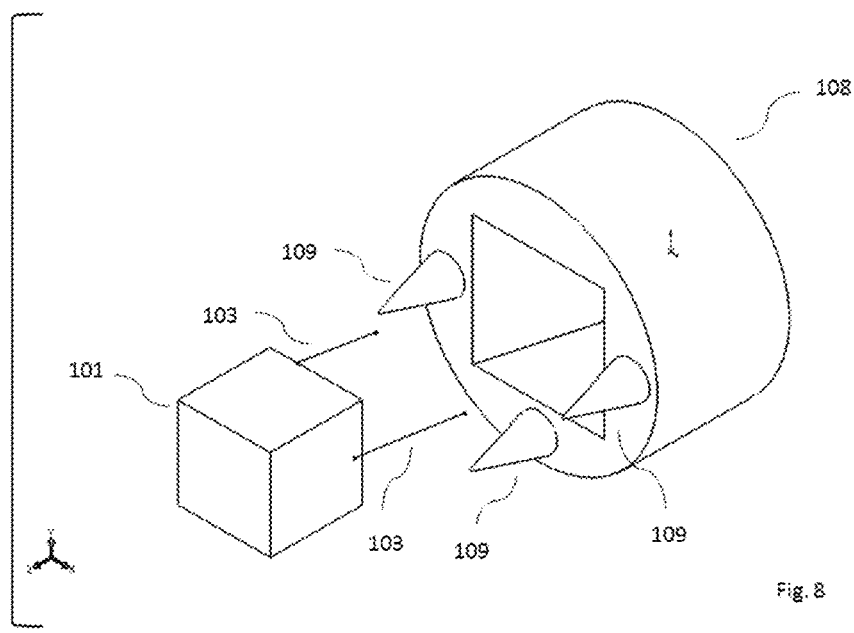
FIG. 8 illustrates a perspective view of subsystem consisting of polymer covered semiconductor material and electrical wires that fit probe with miniaturized electrodes of the first embodiment of the present invention.
Figure 9:
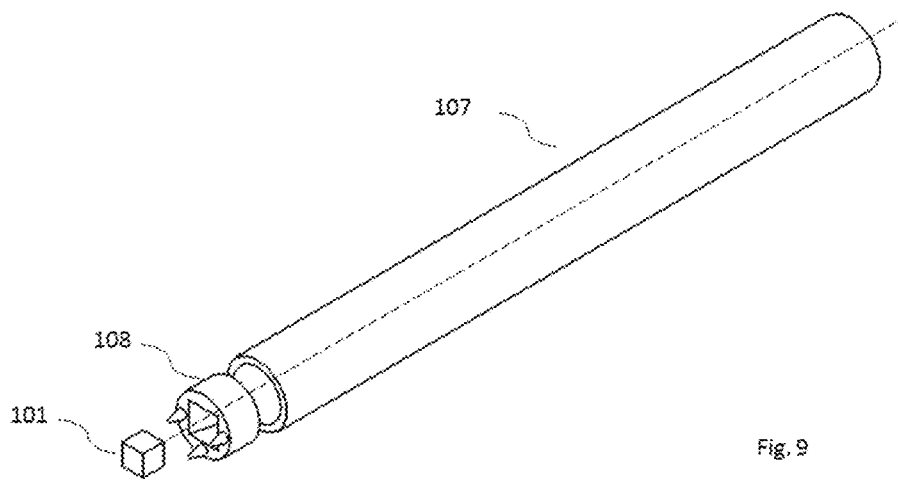
FIG. 9 illustrates a perspective view of subsystem consisting of the polymer covered semiconductor material, probe, and encapsulation containing electrical wire connections to electronic circuits of the first embodiment of the present invention.

FIGS. 2 through 9 illustrate an exemplary but not limiting overview and use of a proprietary subsystem using the polymer covered semiconductor material 101 in FIG. 1 for a first embodiment of the present invention. The semiconductor material is covered with an electrically insulating but thermally conductive medical grade polymer. Electrical wires 103 connect to the semiconductor through a silver paste 102 which facilitates electrical contact and also creates a junction between two dissimilar electrically conductive materials. The polymer covered semiconductor material 101 is in thermal contact with a temperature sensor 104 where thermal contact is ensured through a thermally conductive paste 105. The polymer covered semiconductor material 101 is electrically insulated because of the polymer which is not electrically conductive. Electrical wires for temperature sensor 106 are contained with other such electrical wires in encapsulation 107. The polymer covered semiconductor material 101 is brought to a pre-determined temperature level before it is pushed into a probe 108 configured with miniaturized electrodes 109 of which one is connected to ground (FIG. 13). Two of the miniaturized electrodes are connected to the plus and minus inputs of the instrumentation amplifier contained in the bipolar signal amplifier circuit (FIG. 13) which measures and amplifies the voltage sensed by these miniaturized electrodes. The probe containing the polymer covered semiconductor material 101 and miniaturized electrodes 109 is inserted intra-epidermally into a human patient. The temperature sensor 104 is not inserted into the patient but remains in encapsulation 107 after temperature measurement for the polymer covered semiconductor material 101 has occurred. If the temperature sensor 104 is sufficiently miniaturized such that it is of comparable size to the polymer covered semiconductor material 101 or miniaturized electrodes 109, intra-epidermal insertion into the patient may occur. FIGS. 1 to 9 constitute a subsystem contained in a handheld device acting as a minimally invasive heat stimulus/nerve impulse response measurement tool that serves both to apply a thermal stimulus intra-epidermally in a human patient and measure the neural response of small fibers in the proximity of the stimulus. The measurement isolates the voltage response of small nerve fiber endings local to the stimulus. It is possible to use instead of one probe 108, an array of probes to detect action potential pulses on a first location and a second location on a patient. In this case, the array of probes is capable of determining the time of passage of a nerve action potential pulse as it passes from that first location on the patient to the second location on the patient. All electronic circuits can be battery operated or powered from a plug-in wall power outlet.

Figure 10:
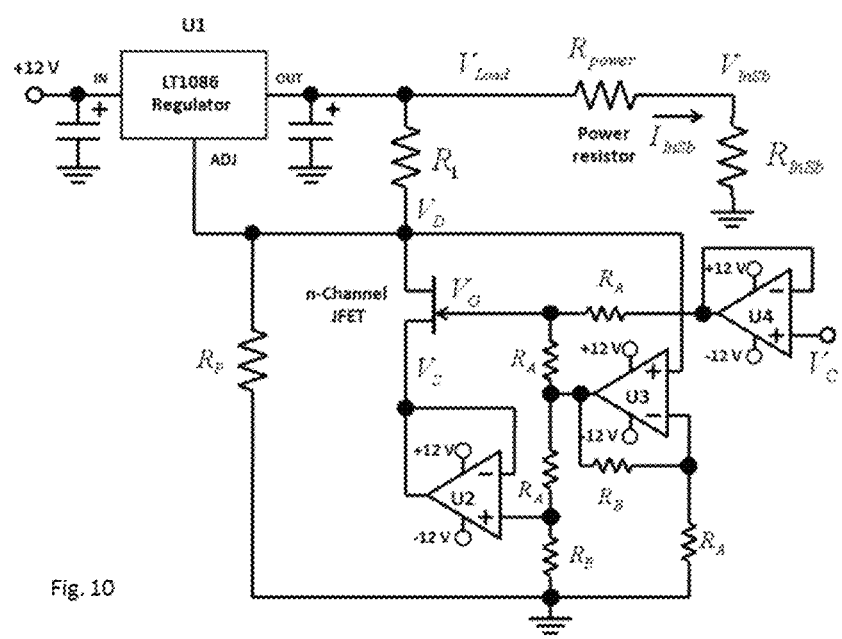
FIG. 10 is a schematic drawing of an electronic circuit that delivers power to the polymer covered semiconductor material.

FIG. 10 illustrates a proprietary use of the Nay-Budak voltage variable resistor electronic circuit with an adjustable voltage regulator. For a description of the referenced circuit see K. Nay, A. Budak, "A Voltage-Controlled Resistance with Wide Dynamic Range and Low Distortion," IEEE Trans. on Circ. and Syst., 30(10), October 1983, pp. 770-772. The adjustable voltage, low dropout (LDO) regulator denoted in FIG. 10 as U1 is shown as an illustrative but not limiting example to be the Linear Technology LT1086. The circuit generates a voltage across the load which consists of power resistor $R_{power}$ and the polymer covered semiconductor material 101. The semiconductor material is modeled as a heat source possessing a resistance denoted as $R_{InSb}$. The voltage drop across the load is denoted $V_{Load}$. This voltage determines the operating temperature achieved by the polymer covered semiconductor material 101. The power resistor limits the current $I_{InSb}$ into the polymer covered semiconductor material 101 preventing overload of the regulator. The voltage $V_{Load}$ is determined by input control voltage $V_C$ which varies the effective resistance between the node having potential $V_D$ and ground. This effective resistance is here denoted as $R_2$. From the data sheet for the LT1086 regulator the voltage drop (expressed in volts) across the load is approximately $$V_{Load} \approx 1.25\left(1 + \frac{R_2}{R_1}\right) \quad \text{(Equation 1)}$$

The part of the circuit in FIG. 10 consisting of the operational amplifiers denoted U2, U3 and U4, the resistors with resistances $R_A$ and $R_B$ along with the n-channel junction field effect transistor (JFET), and the resistor $R_P$ set the resistance $R_2$. This circuit except for $R_P$ is the design for a voltage-variable resistor due to Nay and Budak. The Nay-Budak circuit without resistor $R_P$ yields a resistance between the node at potential $V_D$ and ground that we here denote as $R_{JFET}$. Therefore, we have $$R_2 = R_P \| R_{JFET}. \quad \text{(Equation 2)}$$

Figure 18:
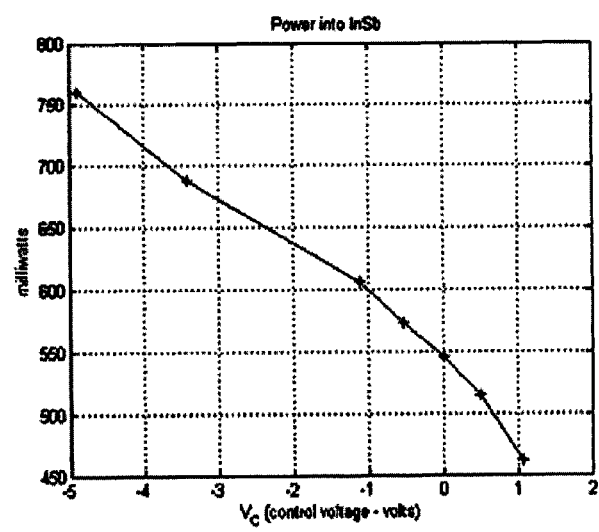
FIG. 18 illustrates a graph of the power that goes into the polymer covered semiconductor material as a function of the input control voltage $V_C$.

The resistor $R_P$ is an improvement upon the Nay-Budak circuit in that it is an effective way to shift the range of possible resistances $R_2$ into a range causing $V_{Load}$ to yield indium antimonide temperatures over a useful non-damaging range for human tissue. Voltage driven materials have shown in our laboratory experiments to generally provide more heat than current driven ones. Indium antimonide and similar types of materials have the advantage that for small sizes resistance is not too small relative to metals of similar size. Unlike in metals, less current is needed in indium antimonide and similar types of materials to produce significant heating making battery power feasible. In support of this, FIG. 18 shows the power that goes into the indium antimonide heat source as a function of the input control voltage $V_C$. For a polymer covered semiconductor material 101 in the material embodiment of doped indium antimonide, an increase in the source voltage results in a drop in the resistance of the indium antimonide. For example, a 10 ohm 25 watts 1% tolerance resistor placed in series with the indium antimonide material allows the flow of a much higher current through the material as compared for example, to having a 100 ohm 0.25 watts resistor in series with the material. The higher power resistor enables pushing power levels up compared to for example, the 100 ohm 0.25 watts resistor. For example, with these settings current values of approximately 0.5 amperes are reached.

Figure 11:
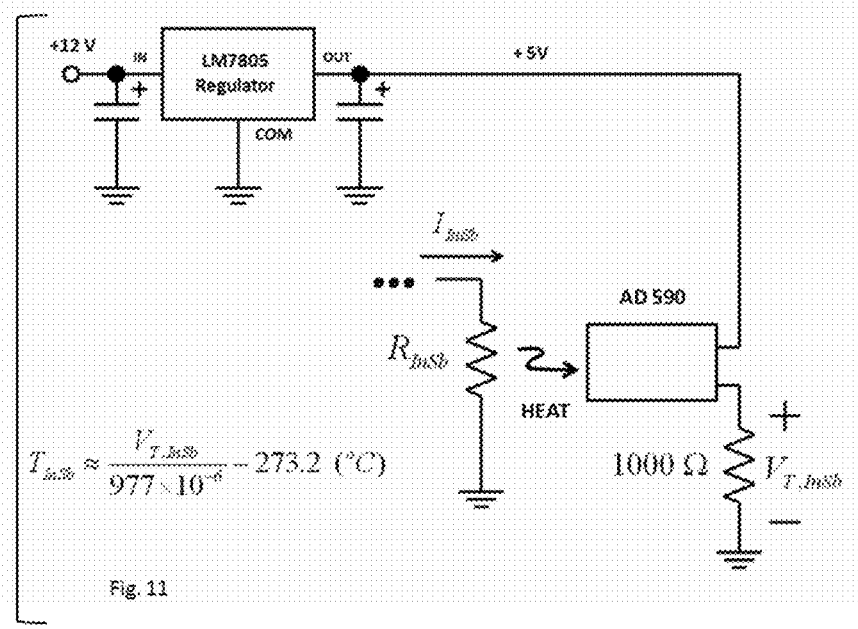
FIG. 11 is a schematic drawing of a typical electronic circuit for measuring the temperature of the polymer covered semiconductor material.
Figure 12:
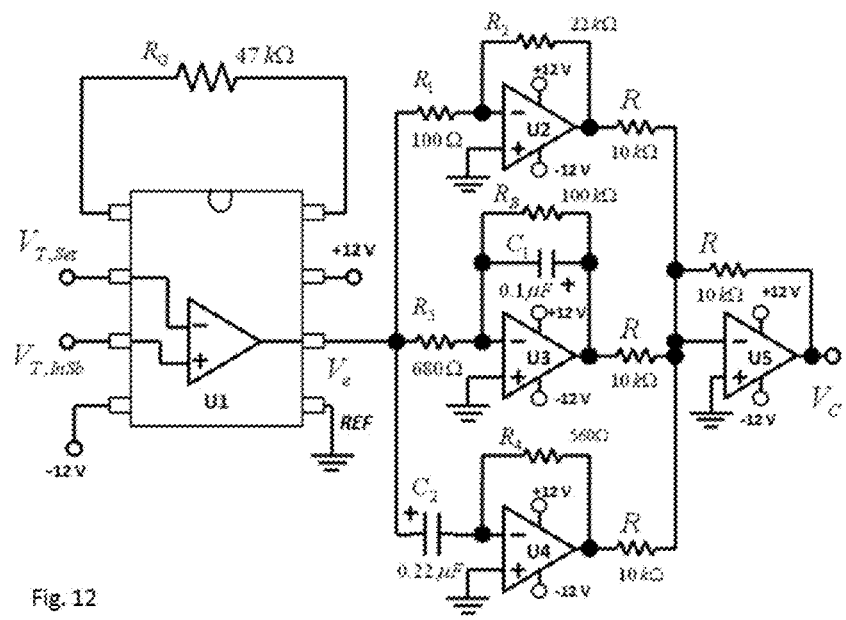
FIG. 12 is a schematic drawing of a typical electronic circuit based on a proportional integral derivative unit for temperature control of the polymer covered semiconductor material.

FIGS. 11 and 12 illustrate exemplary uses of electronic circuitry for the proprietary subsystem for a first and alternate embodiment of the present invention. The choices of electronic components are illustrative but not limiting examples. Temperature measurements are made with a temperature sensor 104 that outputs a voltage via electrical wires for temperature sensor 106 that corresponds to the temperature value it senses. The measured voltage values are then converted to temperature values. Temperature measurement of the polymer covered semiconductor material 101 is performed by using an Analog Devices AD590 2-lead flat-pack temperature sensor denoted 104, and the circuit depicted in FIG. 11. The choice of temperature sensor is illustrative but not limiting. The temperature sensor requires a +5 V dc supply voltage provided for example by an LM7805 fixed voltage regulator. The temperature of the polymer covered semiconductor material 101 is indicated by the voltage drop across the 1000 Ohm resistor denoted by $V_{T,InSb}$. The conversion equation for the temperature indicating voltage drop $V_{T,InSb}$ to temperature in degrees Celsius is indicated in the drawing of FIG. 11. An illustrative but not limiting example listing of components and parts for the circuits in FIGS. 10 and 11 is shown in Table I. The proportional-integral-derivative (PID) control subsystem depicted in FIG. 12 is modeled based on experimentally setting the control voltage $V_C$ via a voltage divider and measuring the corresponding temperature indicating voltage $V_{T,InSb}$. A static linear model was fit to the collected data:

$$V_{T,InSb} = -0.0080 V_C + 0.347 \text{ (Volts)} \quad \text{(Equation 3)}$$

The PID control unit components are chosen to produce a stable feedback control of temperature with an acceptably small steady-state error based on this static linear model. We see that the error signal (voltage) is derived from the output of an instrumentation amplifier (IA): Linear Technology LT1920, where from the specifications $V_e = G(V_{T,InSb} - V_{T,Set})$ and IA gain is G=2.0. The PID control unit was designed, that is component values were determined based on an LTspice IV (Linear Technology) SPICE model (not shown here). The "plant" to be controlled by the PID control unit is defined by the dynamic model of the relationship between $V_C$ and $V_{T,InSb}$. The previous static linear model was modified to include a simple pole to model the time-response of the plant: See the sub-circuit made up of the components labeled as B2, R10, C3 and V4.

TABLE I

| Part | Description | Quantity |
| --- | --- | --- |
| AD59OKF | ±2.5 degree acc. 2-lead flat-pack temperature sensor | 1 |
| LT7805 | 5V regulator | 1 |
| LT1086 | LDO adjustable regulator | 1 |
| 2N5486 | n-channel JFET | 1 |
| LM248 | Quad 741 op amp | 1 |
| 0.68 microFarad | Electrolytic capacitor | 1 |
| 0.22 microFarad | Electrolytic capacitor | 1 |
| 10 microFarad | Electrolytic capacitor | 2 |
| 120 Ohm | ¼ W, 5% resistor | 1 |
| 580 Ohm | ¼ W, 5% resistor | 1 |
| 10 Ohm | 25 W, 1% power resistor | 1 |
| 8.2 KOhm | ¼ W, 5% resistor | 2 |
| 10 KOhm | ¼ W, 5% resistor | 4 |
| 1 KOhm | ¼ W, 5% resistor | 2 |
| 680 Ohm | ¼ W, 5% resistor | 1 |

FIG. 13 illustrates exemplary uses of electronic circuitry for the proprietary subsystem for a first embodiment of the present invention described in previous figures. As such, a typical embodiment of an electronic amplifier for nerve impulse measurements based on the Linear Technology LT1920 instrumentation amplifier (IA) is shown in FIG. 13. The said embodiment is from a design taken from the data sheet for the LT1920 IA (U1) which also makes use of two LT1112 op amps (U2 and U3). The circuit derives its power from the voltage sources V1 and V2 which may range in value from 3 volts to 12 volts (DC). The passband gain of the circuit is nominally 1000 V/V and so therefore $$V_{OUT} = 1000(V_{IN+} - V_{IN-}) \quad \text{(Equation 4)}$$

The passband for the components of FIG. 13 is from about 0.3 Hz to about 5000 Hz (3 dB points). The passband bandwidth is determined mainly by the capacitor $C_3$ and may be reduced by increasing the size of this capacitance. The circuitry in FIG. 13 is used for detecting action potentials (APs) in nerve impulse amplifier outputs obtained as a result of applying a thermal stimulus described in FIGS. 1 through 9 to nerve fibers that respond to such thermal stimuli and by using the electronic circuitry of FIGS. 10 through 12 for a first embodiment of the present invention.

Figure 16A:
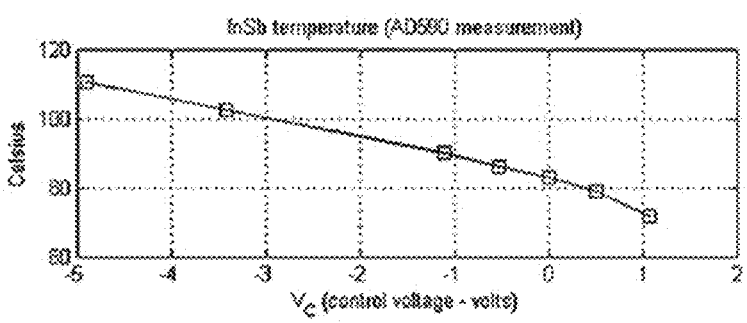
FIG. 16a illustrates indium antimonide material temperature over a range controlled by the input control voltage $V_C$.
Figure 16B:
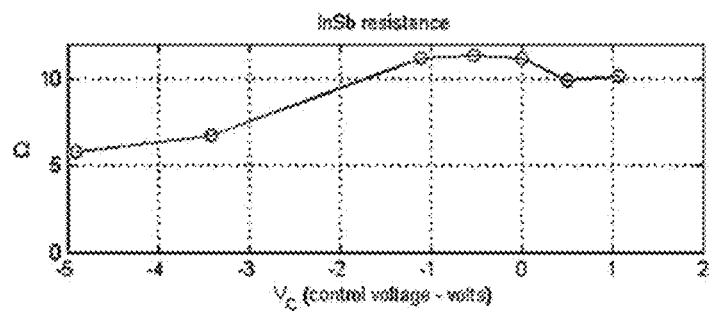
FIG. 16b illustrates how the resistance of the indium antimonide material $R_{InSb}$ varies with control voltage $V_C$.
Figure 17A:
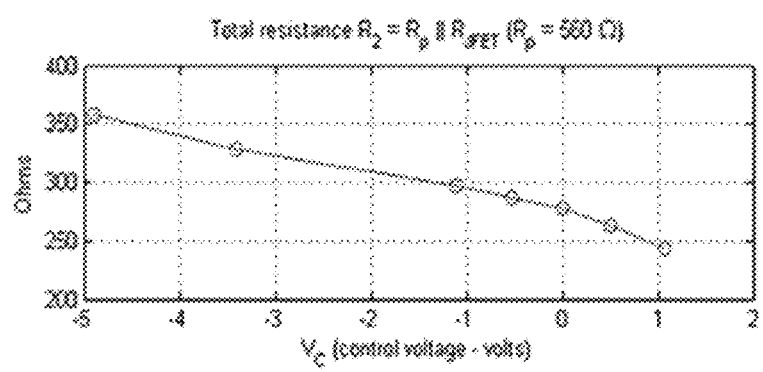
FIG. 17a illustrates the resistance between the node of potential $V_D$ and ground in FIG. 10 as a function of the input control voltage $V_C$.
Figure 17B:
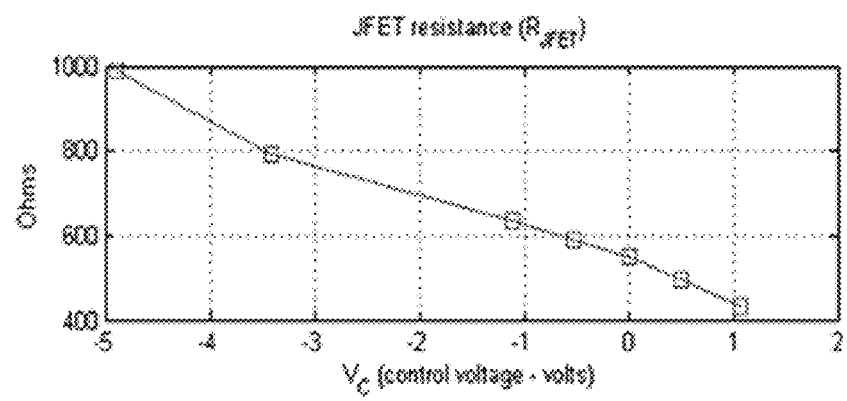
FIG. 17b illustrates the resistance between the node of potential $V_D$ and ground in FIG. 10 excluding the effect of resistor $R_P$ as a function of the input control voltage $V_C$.

FIGS. 16 through 18 show results obtained with the proprietary use of the circuit illustrated in FIG. 10. Depicted power values in FIG. 18 are calculated from measured circuit variables. The advantage of setting $R_2$ via the control voltage $V_C$ instead of mechanically via a potentiometer is that it allows the introduction of an electronic feedback control of the semiconductor heat source temperature. Such a control measures the difference between the heat source temperature and a desired user set-point temperature and automatically adjusts the control voltage $V_C$ to maintain the set-point value in spite of thermal load variations. Another advantage of our invention is that unlike in metals, less current is needed in indium antimonide and similar types of materials to produce significant heating, even in materials measuring microns in size, making battery power feasible. As such, the advantage of the method disclosed in this application is that such devices can be portable and battery operated by a high power density battery. In support of this, see FIG. 18.

The subsystem that is inserted intra-epidermally can be disposable so that it is replaced with each procedure and contains the electrodes input to the nerve impulse amplifier circuit, the semiconductor indium antimonide thermal source also known as the thermal stimulus. It is possible to set up a re-cycling program to reclaim probe materials assuming this is economically meritorious. Electrodes are intended to be disposable, the part that contacts tissue. The electronics will be outside of that part of the device which introduces the electrodes and thermal source into the tissue intra-epidermally for a depth of the order of millimeters. Polymer encapsulation of the semiconductor is for patient electrical isolation but with good thermal conductivity for the tissue. There must be wiring from the electronics module to the electrodes, thermal source and temperature sensor. The wiring is high gauge, meaning rather fine, since current levels and voltages are small. An example embodiment of the temperature sensor is a two-lead device from Analog Devices based on bipolar transistor technology. A commercial implementation of the subsystem would more likely use a thermistor. There are companies that make quite small thermistor devices including for medical applications such as Alpha Technics, or Quality Thermistor, Inc.

The thermal stimulus properly deployed in the intra-epidermal tissue is in adequate proximity to where unmyelinated C fiber neurons are normally located. These neurons will respond to low-level heating in a range that cannot cause a burn generating action potentials (APs) which are sensed by the nerve impulse amplifier electrodes. The latter are in close proximity to the thermal stimulus, being part of the intra-epidermally inserted subsystem. Signals output from the nerve impulse amplifier are used to distinguish the normal from the abnormal neural responses. Surface stimulus with surface signal detection is possible and is already done for other purposes such as deriving neural signals for prosthetics control. However, such surface measurements are more susceptible to interference from external sources such as power lines. This is partly why our subsystem emphasizes intra-epidermal insertion of stimulus and neural response sensing where the stimulus, type of neurons that we desire to characterize and neural response sensing are all in close proximity of each other. Also, the point-source/point-measurement aspect gives spatial resolution to the diagnostic tool. It is possible to design the electronics to limit power flow into the thermal stimulator that tissue burn simply cannot happen. Indeed, the present feedback control unit for temperature is part of this. However a current/voltage limiting circuit may be added for extra safety. Electrical isolation procedures, standard and known, exist to isolate the patient from a failure of the nerve impulse amplifier circuit.

The example experimental data shown in FIGS. 19 through 20 is obtained from detecting action potentials (APs) in nerve impulse amplifier outputs obtained as a result of applying a thermal stimulus described in FIGS. 1 through 9 to certain types of nerve fibers that respond to such thermal stimuli and by using the electronic circuitry of FIGS. 10 through 13 for a first embodiment of the present invention. The experimental data is obtained from earthworm experiments and is processed according to a proprietary algorithm described herein. The algorithm involves the proprietary application of the concept of matched subspace detection (MSD) first described in L. L. Scharf, B. Friedlander, "Matched Subspace Detectors," IEEE Trans. on Signal Processing, 42(8), August 1994, pp. 2146-2157 and adapted to collected earthworm test data where the thermal stimulus was applied close to the miniaturized electrodes 109 that input to the nerve impulse amplifier of FIG. 13. The basic problem the algorithm is solving is to reliably identify nerve action potential pulses in the presence of random noise signals and most importantly in the presence of interference due to power line hum which has a fundamental frequency of 60 Hz. The matched subspace detection (MSD) theory of Scharf and Friedlander models the samples of a signal as the sum of: a. random noise [zero-mean, white Gaussian noise (WGN)], b. the desired signal and c. deterministic (that is, non-random) interference. Projection operators in the form of matrices are used to form signal detection statistics while suppressing the interference that may be present degrading the detection of the desired signal, which for us is nerve action potentials (APs). Various specific signal detectors are discussed in the Scharf and Friedlander paper and we choose the method described in Section VIII, which is summarized here.

We assume that an N-sample segment of data is contained in the column vector $y \in \Re^N$ and this data is explained by one of two statistical hypotheses:

$$H_0: y = S\phi + \eta$$

$$H_1: y = H\theta + S\phi + \eta \qquad \text{(Equation 5)}$$

The problem here is to decide which of the two hypotheses in the Scharf and Friedlander paper is the most likely hypothesis to explain the data contained in y. Under the null hypothesis $H_0$ the samples y column vector contains only the interference vector $S\phi$ and the random noise vector $\eta \sim N(0, \sigma^2 I)$ (I is the N×N identity matrix). The vector $\eta \in \Re^N$ is of 0-mean, mutually uncorrelated Gaussian random variables each possessing a variance of $\sigma^2$. The matrix $S \in \Re^{N \times t}$ models the interference as a linear combination of basis vectors (the individual t columns of S), and so the coordinates of this representation of the interference are in the column vector $\phi \in \Re^t$. For our situation N is not very big in relation to the length of the entire nerve impulse amplifier output samples sequence, where such sequence is typically 100 ms long containing over 800,000 samples. The power line hum interference changes relative slowly over N samples, and so may be considered to be effectively constant within any given data segment y. On this assumption a reasonable choice for matrix S is $$S = [11 \ldots 1]^T \in \Re^{N \times 1} \text{ (that is, } t=1\text{)} \qquad \text{(Equation 6)}$$

Now, by contrast under the alternative hypothesis $H_1$ the data in y is assumed to be explained by the interference and random noise and also the presence of a signal term $H\theta$. Similarly, to matrix S the columns of $H \in \Re^{N \times p}$ when linearly combined by the coordinates in $\theta \in \Re^p$ represent the signal, which for us is a single AP pulse. We assume that $H = h \in \Re^{N \times 1}$ is a single column vector the samples (elements) of which represent the shape of a single AP pulse. In practice, this desired shape is determined by examining the actual data to view what are believed to be single AP pulse events. We use piecewise linear fitting to arrive at appropriate elements of h. FIG. 19 illustrates this approach. The bottom-most subplot of FIG. 19 shows the solid lines representing piecewise linear fitting whose samples N=75 constitute the elements of h and so are a template pulse that we assume is adequately representative of every action potential pulse in the original 800,000 sample data record. We mention that we downsample the original data by factor D to avoid having to work with very big matrix operations to compute the action potential pulse detection statistic—see equation 7 below. If D is too small then N is too big and the computations proceed far too slowly. On the other hand, D must not be so big as to degrade the quality of the samples to the point where they no longer represent the AP pulses that we seek.

The statistical signal processing theory which is an extension of the concept of the generalized likelihood ratio (GLRT) test in the Scharf and Friedlander paper concludes in Section VIII that the detection of an AP pulse should be based on using the test statistic $$L_2(y) = (N-2)\frac{y^T P_S^\perp P_G P_S^\perp y}{y^T P_S^\perp P_G^\perp P_S^\perp y} \in \mathfrak{R} \text{ (but is non-negative)} \quad \text{(Equation 7)}$$

Of all the options considered in the Scharf and Friedlander paper we specifically choose equation 7 because it involves making the fewest prior assumptions about the signal and interference in a data segment. It is shown in the Scharf and Friedlander paper that the random variable in equation 7 has a distribution that is either a central (null hypothesis) or non-central (alternative hypothesis) F-statistic. This knowledge can in principle be used to rationally select a detection threshold based on an acceptable false alarm rate for pulse detection. That is, we only consider $L_2(y)$ to have indicated the presence of an action potential pulse in $y \in \mathfrak{R}^N$ if $L_2(y)$ is big enough.

The matrix operations in equation 7 involve projection operators which are defined as follows:

$$P_S^\perp = I - S(S^T S)^{-1} S^T \in \mathfrak{R}^{N \times N}$$

$$P_G = P_S^\perp H (H^T P_S^\perp H)^{-1} H^T P_S^\perp, \text{ and } P_G^\perp = I - P_G \in \mathfrak{R}^{N \times N} \quad \text{(Equation 8)}$$

The detailed rationale for the matrices in equation 8 is somewhat involved and will not be considered here (see the Scharf and Friedlander paper). However, it may be worth mentioning that matrix-vector product $P_S^\perp y$ effectively removes the interference component from segment y by the projection of y onto the subspace of vector space $\mathfrak{R}^N$ that is complementary to the interference subspace defined by the columns of S. It is in this way that the otherwise destructive impact of power line hum interference is mitigated.

The statistical test of equation 7 is applied in sliding window fashion to the entire downsampled data record. The results of this operation applied to FIG. 19 data are depicted in FIG. 20a. A detection threshold was also applied to the time-series of statistics $L_2(y)$. More specifically, data segment $y \in \mathfrak{R}^N$ is considered to contain an action potential pulse if $L_2(y) \geq 100$ and this result is seen in FIG. 20a. The threshold value of 100 used here was chosen by subjective judgment. The lines in the last subplot of FIG. 20a show the time-series of action potential pulse where 1 indicates the presence of the action potential pulse and 0 indicates the absence of the action potential pulse.

Additional processing is needed to study the time-relationship between detected action potential pulses. For example, Gerstner and Kistler (see W. Gerstner, W. M. Kistler, *Spiking Neuron Models: Single Neurons, Populations, Plasticity*, Cambridge University Press, 2002) explain that the information in action potentials is conveyed not by specific action potential pulse shapes or their amplitudes but rather by the timing relationship of pulses. This point is also conveyed by Izhikevich (see E. M. Izhikevich, *Dynamical Systems in Neuroscience: The Geometry of Excitability and Bursting*, The MIT Press, 2007).

Figure 20A:
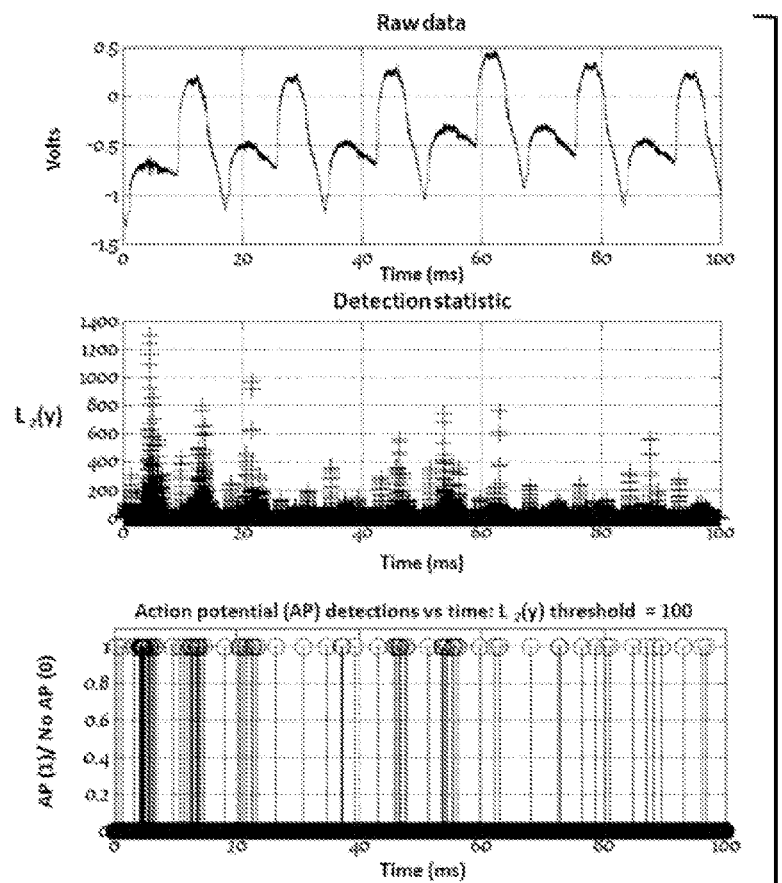
FIG. 20a presents three graphs representing processed experimental data obtained from a first embodiment of the present invention.
Figure 20B:
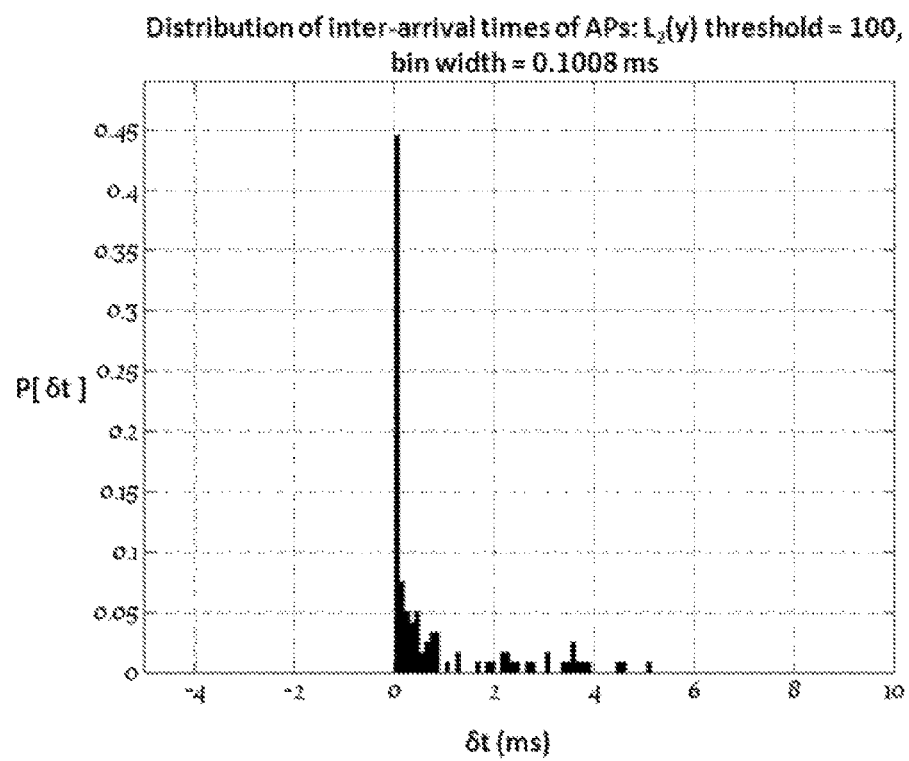

If the jth action potential pulse occurs at time $t_j$ and the next action potential pulse, the (j+1)th action potential pulse occurs at time $t_{j+1}$ then the inter-arrival time is $\delta t_j = t_{j+1} - t_j$. The time of occurrence of the action potential pulses is seen in the bottom plot of FIG. 20a and so the inter-arrival times are easily determined. FIG. 20a represents processed experimental data obtained from a first embodiment of the present invention: (top) a subplot of the downsampled data first seen in FIG. 19b; (middle) a subplot of the time-series of detection statistics from the computation described in equation 7; (bottom) a subplot showing the results of applying a detection threshold to the data in the middle subplot so that the lines are of action potential pulse where 1 indicates pulse presence and 0 indicates pulse absence. The shown data is processed according to a proprietary algorithm. FIG. 20b represents processed experimental data obtained from a first embodiment of the present invention and consists of an empirical distribution of the action potential pulse inter-arrival times for the data in FIG. 20a.

Figure 19A:
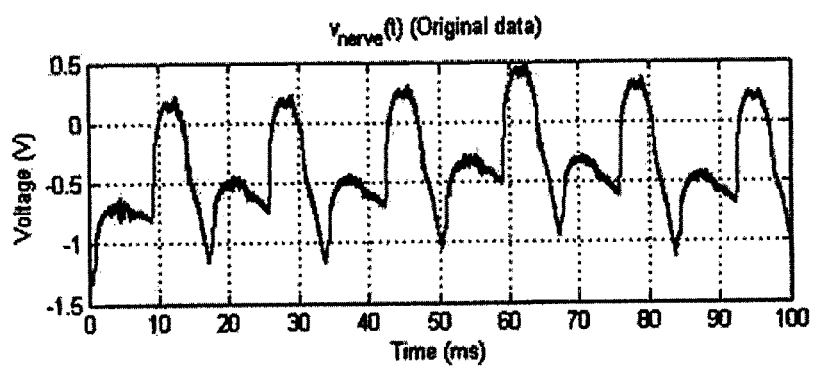
FIG. 19a illustrates experimental data obtained from the first embodiment of the present invention showing the raw signal data from nerve impulse amplifier outputs from earthworm experiments where the thermal stimulus was applied close to the electrodes and the line is the original, raw data.
Figure 19B:
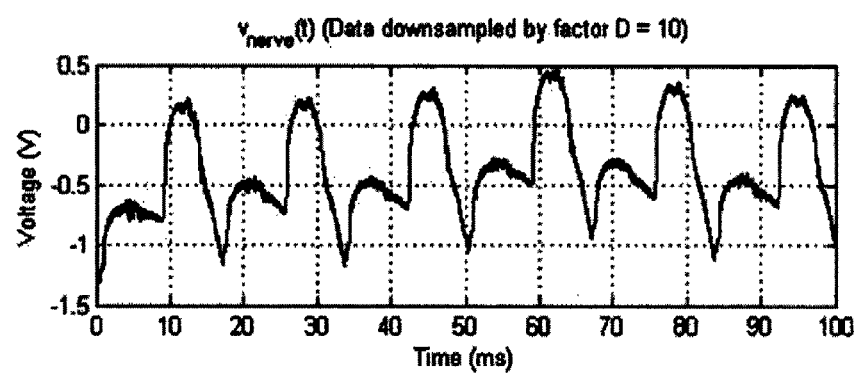
FIG. 19b illustrates experimental data obtained from the first embodiment of the present invention showing the raw signal data from nerve impulse amplifier outputs from earthworm experiments where the line is the same data as in FIG. 19a merely downsampled by a factor of D=10.
Figure 19C:
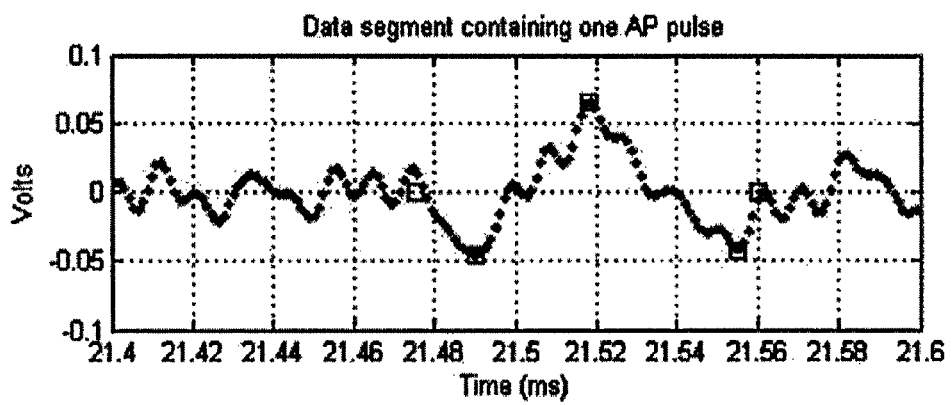
FIG. 19c shows a segment of downsampled data containing a single action potential pulse.
Figure 19D:
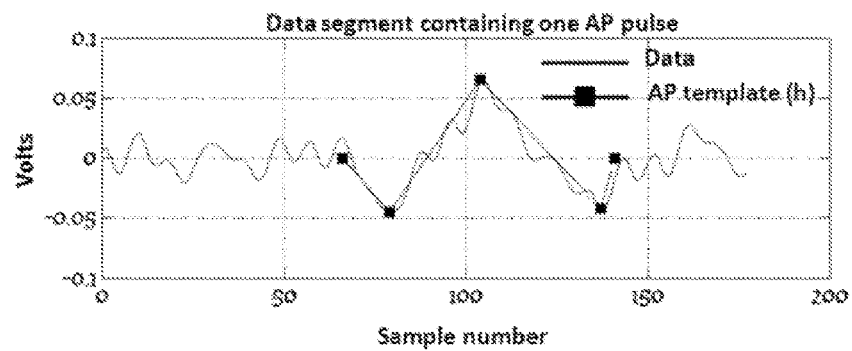
FIG. 19d shows a segment of downsampled data where solid lines are the piecewise linear model for the action potential pulse (here N=75 samples long). The shown data is processed according to a proprietary algorithm.

The sampling period for the original raw data of FIG. 19a is $T = 1.12 \times 10^{-4}$ milliseconds. With downsampling by a factor of D=10 the new sampling rate is $T_D = 1.12 \times 10^{-3}$ milliseconds. Since the template action potential pulse in FIG. 19c,d is N=75 samples the duration of the template pulse is $NT_D = 0.084$ milliseconds. We see in FIG. 20b that the bin widths in the histogram are about 0.1 milliseconds, and so the bin size is about as small as it is reasonable to choose given the assumed duration of an action potential pulse.

Figure 21:
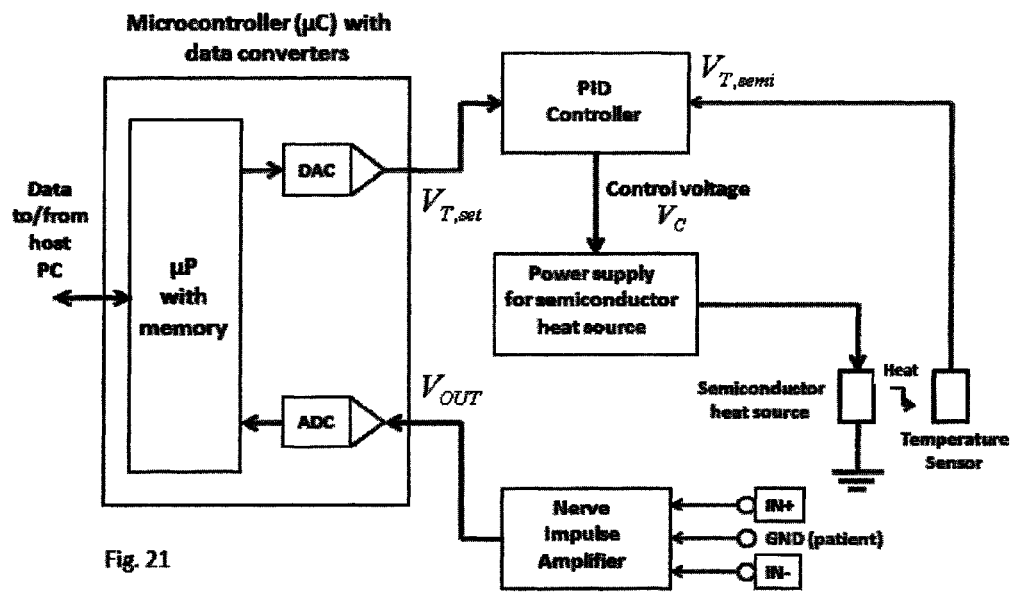
FIG. 21 illustrates a microcontroller interface between the heat stimulus/nerve impulse response measurement system and a host personal computer.

There is a need to control the thermal stimulus/nerve impulse response measurement subsystem described in FIGS. 1 through 9 and the accompanying electronics in FIGS. 10 to 13 that drives the system and records nerve impulse responses. This is because such a subsystem is an analog subsystem that requires digital control. FIG. 21 illustrates such a microcontroller interface between the subsystem depicted in FIGS. 1 to 13 to a host personal computer (PC). The microcontroller (μC) is a self-contained (1-chip) way to achieve this and is comprised of a microprocessor (μP) with memory for program store, data storage, a digital-to-analog converter (DAC), and an analog-to-digital converter (ADC). We should have two of each of an ADC and a DAC to support a 2-point diagnostic probing which is an extended method of diagnostic testing where one thermal stimulus and two probes with electrodes are used such that the probes with electrodes are placed at two different locations on the patient. The microcontroller should also contain a time-keeping device for time-stamp collected data because action potential pulse timing with respect to time of application of stimulus is important diagnostic information. Depending on the type of microcontroller, it should also comprise a serial interface to support USB port to the host computer, or wireless communications, for example Bluetooth to a smartphone. Note that a single-chip solution is necessary to conserve space and power since battery operation in a hand-held system is much desired. The microcontroller can control the device and report diagnostic information to a host PC. Commands are issued to a digital-to-analog (D/A) converter DAC to control applied temperature via an applied voltage vs. time. The DAC outputs a set-point voltage $V_{T,set}$ according to a μP command that determines the desired temperature of the semiconductor heater and this voltage may even vary with time. The analog feedback control based on the proportional-integral-derivative (PID) method uses a temperature sensor measurement $V_{T,semi}$ to ensure that the temperature of the heater tracks the set-point. Nerve response vs. time is sampled by an analog-to-digital (A/D) converter ADC and this data must be collected, saved and processed to extract diagnostic information. The ADC converts the output voltage $V_{OUT}$ from the nerve impulse amplifier into a binary number, for example 10 to 12 bits which the μP reads in and saves to its own local memory. When a block of data of sufficient size, for example a 0.1 s (second) block of samples is accumulated it may be processed by the μC to characterize the nerve impulses, for example the time relationship between pulses. Such processing may include the de-humming signal processing. The result of the processing may be communicated to the host PC, for example via a USB connection. Instead of the host device, raw data may be uploaded to the host device consisting of a PC or a smartphone for processing to extract the diagnostic information.

Figure 22:
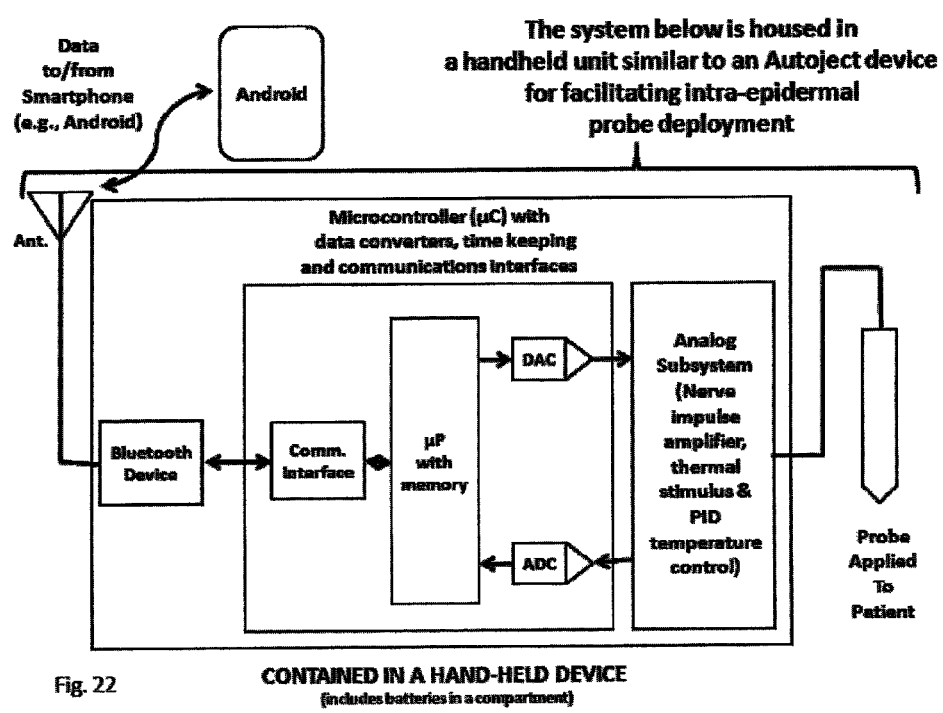
FIG. 22 depicts the system level architecture, in particular the role of a microcontroller in a diagnostic tool system for small fiber neuropathy.

The role of a microcontroller as a place for data processing in a diagnostic tool for small fiber neuropathy is shown further in FIG. 22. FIG. 22 depicts the overall architecture and the interface to a smartphone shown here to be Android as an example. Neither a PC/laptop or a smartphone can interface directly with the analog subsystem, hence the use of a microcontroller or like entity is unavoidable. At the very least, the microcontroller is needed to execute the appropriate time sequence of stimulus application and response recording. In principle, operation is initiated automatically when the probe subsystem of FIGS. 1 through 9 is introduced into the patient, without the temperature sensor 104, as discussed above.

Microcontrollers likely offer enough computational power to do the necessary data processing as well as data collection. If the microcontroller collects and processes data then only a short message, the diagnostic result need be communicated to the outside world. This limits power consumption in data transmission and conserves battery power. It also eliminates the need for elaborate error control coding. A simple error-detection code with repeat transmission in the event of error is all that would be needed.

Alternate Embodiment

Specific mechanical details of the alternate embodiment are exemplary and are not limiting.

Figures 15A, 15B, 15C:
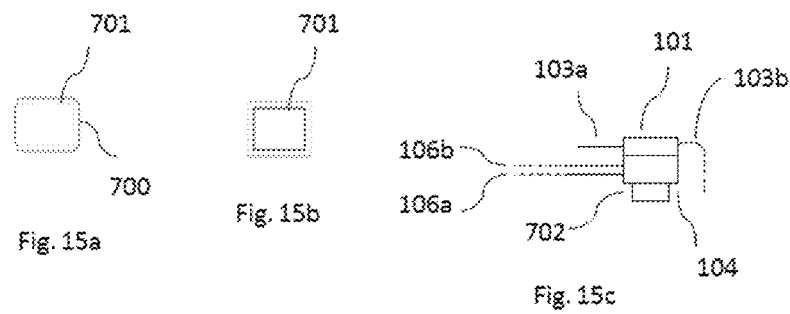
FIG. 15a is a front view of cap and opening fitted to cover groove at clamp tip in FIG. 14a of an alternate embodiment of the present invention.
FIG. 15b is a left side view of FIG. 15a of an alternate embodiment of the present invention.
FIG. 15c is a front view of the main parts of a thermal system of an alternate embodiment of the present invention.

FIGS. 14a, b, c through FIGS. 15a, b, c illustrate an exemplary but not limiting proprietary subsystem for an alternate embodiment of the present invention. FIG. 14a shows a top view of an exemplary alternate embodiment of a rod constituting half of clamp 600 holding in groove 603 at clamp tip 604 the polymer covered semiconductor material 101, temperature sensor 104, and a magnet 702 when additional thermomagnetic control over temperature is preferred. Placement of the magnet 702 results in a magnetic field concentration along a perpendicular direction to electric current flow such as the exemplary y-direction of the Cartesian coordinate system depicted in FIG. 8. In the presence of an applied voltage or current to the polymer covered semiconductor material 101, Nernst-Ettingshausen and Righi-Leduc thermomagnetic effects may take place in the material, creating additional heating in the material. Alternative embodiments for this type of material can be compounds from combinations of elements from neighboring groups to III or V in the periodic table of elements. Some nanoengineered materials such as ceramics are also alternative embodiments. More heat is generated in a smaller size material partly due to the smaller cross sectional area of the material, and partly due to the properties of the material itself.

Electrical wires for temperature sensor 104 and electrical wires for temperature sensor 106 are contained in through-hole 602 reaching the groove 603. A clamp is configured with two halves of which the first one is shown in FIGS. 14a, b, c. The second half of the clamp is fastened onto the first by using hole 601. The clamp tip 604 is covered with a protective removable cap 700, depicted in FIGS. 15a,b, and is made of an electrically insulating but thermally conductive medical grade plastic that can be sterilized in an autoclave or disposed of. The polymer covered semiconductor material 101 displays particular thermal properties under specific experimental conditions obtained with specified electronic circuits described herein, achieving a collagen denaturing effect in biological tissue. The tissue is heated slowly while the heating temperature is maintained at an optimum value causing the tissue to lose fluid. Tissues subjected to this treatment shrink from dehydration and coagulate while gently heated without burning or scarring the surrounding tissue. The removable cap 700 provides sterilized contact with a patient's tissue and also avoids sending an electrical current through the tissue or patient.

References

1. U.S. Pat. No. 7,912,536 B2, Mar. 22, 2011, C. Fendrock, NeuroMetrix Inc., "Disposable, Multi-Purpose, Cardiovascular, Autonomic, Neuropathy Testing Device".
2. US 2008/0004622 A1 J. Coe et al. "Band Ligation and Coagulation"
3. US 2010/0179524 A1 J. G. Whayne et al. "Method and Devices for Performing Biatrial Coagulation"
4. U.S. Pat. No. 4,512,343 4/1985 E. Falk et al. "Medical Coagulation Device"
5. U.S. Pat. No. 5,207,675 A 4/1993 J. Canady "Surgical Coagulation Device"
6. U.S. Pat. No. 5,599,350 A 2/1997 D. R. Schulze "Electrosurgical Clamping Device with Coagulation Feedback"
7. U.S. Pat. No. 7,044,950 B2 5/2006 T. Yamamoto "High Frequency Coagulation Apparatus"
8. H. Okumura, S. Yamaguchi, H. Nakamura, K. Ikeda, K. Sawada, "Numerical Computation of Thermoelectric and Thermomagnetic Effects", IEEE $17^{th}$ International Conference on Thermoelectrics 1998, pp. 89-92.
9. K. Nay, A. Budak, "A Voltage-Controlled Resistance with Wide Dynamic Range and Low Distortion," IEEE Trans. on Circ. and Syst., 30(10), October 1983, pp. 770-772.
10. L. L. Scharf, B. Friedlander, "Matched Subspace Detectors", IEEE Trans. on Signal Proc., 42(8), August 1994, pp.2146-2157.
11. N. I. Maluf, E. L. McNutt, S. Monroe, D. L. Tanelian, G. T. A. Kovacs, "A Thermal Signal Generator Probe for the Study of Neural Thermal Transduction", IEEE Trans. on Biomed. Eng., 41 (7), July 1994, pp. 649-655.
12. Z. Sun, H. Ying, J. Lu, B. Bell, D. F. Cowan, M. Motamedi, IEEE Transactions on Ultrasonics, Ferroelectrics, and Frequency Control vol. 46, no. 5, September 1999. All pages.
13. N. Massarweh, N. Cosgriff, D. P. Slakey, "Electrosurgery: History, Principles, and Current and Future Uses", Journal of American College of Surgeons, doi:10.1016/j.jamcollsurg.2005.11.017. All pages, published by Elsevier Inc.
14. http://en.wikipedia.org/wiki/Czochralski process
15. W. Gerstner, W. M. Kistler, *Spiking Neuron Models: Single Neurons, Populations, Plasticity*, Cambridge University Press, 2002
16. E. M. Izhikevich, *Dynamical Systems in Neuroscience: The Geometry of Excitability and Bursting*, The MIT Press, 2007

We claim:

1. A probe for assessing nerve function in small-fiber nerve nociceptors in a patient's epidermis, the probe comprising:
   a probe body having a tip, the tip having a size and shape for insertion intra-epidermally into the patient's skin;
   an electrical power source;
   a heat source electrically coupled to the electrical power source and disposed at the tip of the probe so as to conduct thermal energy into an intra-epidermal region of the patient's skin, the heat source electrically insulated so as to isolate the patient from the power source;

at least one electrode disposed at the probe tip; and the at least one electrode disposed so as to detect action potential pulses generated by small-fiber nerves in response to being heated by the heat source.

2. The probe for assessing nerve function in small-fiber nerve nociceptors in a patient's epidermis of claim 1, wherein the heat source comprises a thermistor.

3. The probe for assessing nerve function in small-fiber nerve nociceptors in a patient's epidermis of claim 1, wherein the heat source has a negative temperature coefficient.

4. The probe for assessing nerve function in small-fiber nerve nociceptors in a patient's epidermis of claim 1, wherein the heat source comprises an indium antimonide heating element.

5. The probe for assessing nerve function in small-fiber nerve nociceptors in a patient's epidermis of claim 1, wherein the heat source comprises a heating element and at least one magnet disposed to apply a magnetic field to the heating element.

6. The probe for assessing nerve function in small-fiber nerve nociceptors in a patient's epidermis of claim 1, wherein the heat source comprises a heating element enclosed in an insulator coating.

7. The probe for assessing nerve function in small-fiber nerve nociceptors in a patient's epidermis of claim 1, wherein the tip is disposable.

8. The probe for assessing nerve function in small-fiber nerve nociceptors in a patient's epidermis of claim 1, further comprising:

a temperature sensor disposed in the probe adjacent to the heat source so as to sense the temperature of the heat source; and a feedback circuit in electrical communication with the temperature sensor and a heater control circuit, the heater control circuit in electrical communication with the heat source so as to control the temperature of the heat source.

9. The probe for assessing nerve function in small-fiber nerve nociceptors in a patient's epidermis of claim 8, wherein the heater control circuit comprises:

a voltage regulator having a power input, a power output, and a feedback input, the power output electrically coupled to the heat source;

a power source coupled to the regulator power input;

a feedback element electrically coupled between the regulator output and the regulator feedback input and defining a feedback node;

an resistor coupled between the regulator feedback input and ground;

an active circuit electrically coupled between the regulator feedback node and ground; and a control input coupled to the active circuit, the active control circuit controllable drawing feedback current from the feedback node in response to a signal on the control input.

10. The probe for assessing nerve function in small-fiber nerve nociceptors in a patient's epidermis of claim 1, wherein the power source is a DC power source.

11. The probe for assessing nerve function in small-fiber nerve nociceptors in a patient's epidermis of claim 10, where the power source is a battery.

12. A system for assessing small fiber neuropathy in a patient, comprising:

a probe having a tip comprising a heat source and at least one sensing electrode, the tip configured to penetrate the patient's skin;

a sampling circuit electrically coupled to the sensing electrode and configured to acquire a plurality of samples of electrical output from the at least one sensing electrode; and a sample processing circuit to detect a plurality of action potential pulses from the sensing electrode samples, and then to determine a time relationship between two of the action potential pulses from among the plurality of action potential pulses.

13. The system for assessing small fiber neuropathy in a patient of claim 12, wherein the at least one sensing electrode comprises a plurality of sensing electrodes disposed so as to encircle the heat source.

14. The system for assessing small fiber neuropathy in a patient of claim 12, further comprising a control circuit having a controllable voltage source electrically coupled to the heat source and configured to heat the heat source to a temperature of at least 40 degrees Celsius and less than 46 degrees Celsius.

15. The system for assessing small fiber neuropathy in a patient of claim 12, wherein the sampling circuit further comprises a digital-to-analog converter electrically coupled to the at least one sensing electrode to digitally sample the electrical output from the at least one sensing electrode.

\* \* \* \* \*